| United States Patent [19] | [11] | 4,130,566 |
|---|---|---|
| Hibino | [45] | Dec. 19, 1978 |

[54] PROCESS FOR PRODUCING 5-CARBOXY-2-ACETYLTHIOPHENE

[75] Inventor: Toshihiko Hibino, Takarazuka, Japan

[73] Assignee: Sumitomo Chemical Company, Limited, Osaka, Japan

[21] Appl. No.: 847,063

[22] Filed: Oct. 28, 1977

[51] Int. Cl.² ................................................ C07D 333/24
[52] U.S. Cl. ............................................... 260/332.2 C
[58] Field of Search ................ 260/332.2 C, 332.3 R, 260/523 R

[56] References Cited

PUBLICATIONS

Hartough, "Thiophene and Derivatives," (1952), p. 329.

*Primary Examiner*—A. Siegel
*Attorney, Agent, or Firm*—Wenderoth, Lind & Ponack

[57] ABSTRACT

5-Carboxy-2-acetylthiophene, which is useful as an intermediate for the production of a therapeutic agent, can be prepared in a high yield by the selective oxidation of 5-acetyl-2-thienylacetic acid or its derivative with a particularly selected oxidizing agent, i.e. chromic anhydride complex, dichromate or hypohalite.

9 Claims, No Drawings

PROCESS FOR PRODUCING 5-CARBOXY-2-ACETYLTHIOPHENE

The present invention relates to a process for producing 5-carboxy-2-acetylthiophene.

5-Carboxy-2-acetylthiophene has been known to be a useful intermediate for the production of the thienylthiazole derivative of the formula:

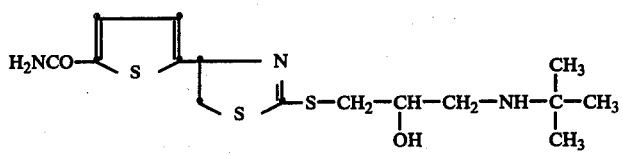

which is useful as a potent therapeutic agent for the treatment of heart diseases such as arrhythmia and coronary heart diseases (U.S. Pat. No. 3,932,400).

With respect to the preparation of 5-carboxy-2-acetylthiophene, there have been proposed the following processes:

(1) Hydrolysis of 5-cyano-2-acetylthiophene, [Linstead, Noble and Wright; J. Chem. Soc., 1937, 911. Dann; Ber., B76, 419 (1943)]

(2) Oxidation of 2,5-diacetylthiophene, [Hartough and Kosak; J. Am. Chem. Soc., 69, 1012 (1947)]

(3) Acylation of thenoic acid ester, [K. Schöegel and H. Pelonsek; Ann., 1 (1962)]

(4) Carboxylation of 2-methyl-2'-thienyl-1,3-dioxolane(acetylthiophene ketal). [Thames and McClesky; J. Heterocyclic Chem., 3, (1), 104 (1966)]

These known processes are, however, unsatisfactory for the commercial production of said compound.

As the result of study, it has now been found that 5-carboxy-2-acetylthiophene can advantageously be prepared in a high yield by the selective oxidation of 5-acetyl-2-thienylacetic acid or its derivative with a chromic acid derivative or a hypohalite.

So far, it has been quite difficult, or rather impossible to expect whether oxidation occurs at the acetyl methyl group or at the methylene group linked to the thiophene ring when 5-acetyl-2-thienylacetic acid or its derivative is subjected to the oxidation reaction.

According to the present invention, however, 5-carboxy-2-acetylthiophene can advantageously be prepared by the selective oxidation of the methylene group linked to the thiophene ring of 5-acetyl-2-thienylacetic acid or its derivative. Specifically, 5-carboxy-2-acetylthiophene can be prepared by the oxidation of 5-acetyl-2-thienylacetic acid, which has the following formula (II):

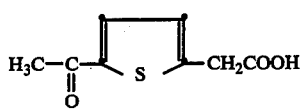

(II)

with a chromic anhydride-solvent complex or a dichromate, or by the oxidation of a compound of the formula (III):

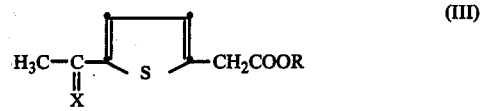

(III)

wherein X is a conventional carbonyl protecting group, and R is a conventional ester residue, with a hypohalite.

The term "conventional carbonyl protecting group" as used herein means any carbonyl protecting group which does not disturb the progress of the oxidation reaction and which is removable. Examples of such carbonyl protecting group are ketal, hemithioketal, dithioketal, thiazolidine, imidazolidine and oxazolidine. The term "conventional ester residue" means any ester residue which does not disturb the progress of the oxidation reaction. Examples of such ester residue are lower alkyl (e.g. methyl, ethyl, etc.) and phenyl groups.

With respect to the oxidation of 5-acetyl-2-thienylacetic acid with said chromic acid derivatives, it can generally be conducted in a solvent at a temperature from 0° C. to the boiling point of the solvent employed, preferably 0° to 100° C.

Examples of preferred chromic anhydride-solvent complex are chromic anhydride-acetic acid complex, chromic anhydride-pyridine complex, chromic anhydride-dimethylformamide complex and the like. Examples of preferred dichromate are potassium dichromate, sodium dichromate, etc.

In carrying out the process using said chromic anhydride-solvent complex, the use of the solvent which, together with chromic anhydride, forms the chromic anhydride-solvent complex is particularly preferable, but the process can also be carried out in other inert solvents such as dichloromethane, carbontetrachloride and hydrocarbons such as light petroleum and petroleum benzine.

While, when a dichromate is used, the process can be carried out in organic acid solvents, water or a mixture thereof. Examples of preferred organic acid solvents are aliphatic acids or anhydrides thereof such as acetic acid, propionic acid, butyric acid, or acetic anhydride.

The chromic anhydride-solvent complex and the dichromate may be used in an amount of 2 to 3 moles per 1 mole of 5-acetyl-2-thienylacetic acid.

It is particularly advantageous to conduct the process in the following manner:

(1) by adding chromic anhydride to acetic acid, acetic anhydride or a mixture thereof to give chromic anhydride-acetic acid complex, (2) adding thereto 5-acetyl-2-thienylacetic acid, and then (3) reacting them at a room temperature for several hours. In this case, the oxidation reaction proceeds completely to give only 5-carboxy-2-acetylthiophene as the product.

With respect to the oxidation of a compound of the formula (III) with a hypohalite, the process can be conducted in a mixture of water and an alcohol (e.g.

methanol, ethanol, etc.) at a temperature from 0° to 60° C. and then removing the carbonyl protecting group.

Examples of preferred hypohalite are sodium hypochlorite, sodium hypobromite, potassium hypochlorite and potassium hypobromite.

In carrying out the process, it is preferable to use at least 3 moles of a hypohalite per 1 mole of the compound of the formula (III).

After the reaction is finished, the carbonyl protecting group can be removed by a conventional method as disclosed in McOMIE; "Protective Groups in Organic Chemistry", Plenum Press London and New York, (1973). For example, ketal, hemithioketal, oxazolidine and imidazolidine can be removed by treating them with a dilute acid such as dil. hydrochloric acid, dil. sulfuric acid, aqueous acetic acid, etc. [C. Djerassi, F. Batres, J. Romo and G. Rosenkranz; J. Am. Chem. Soc., 74, 3634 (1952). E. P. Goldberg and H. R. Nace; J. Am. Chem. Soc., 77, 359 (1955). H. W. Wanzlict and W. Loechell; Chem. Ber., 86, 1463 (1953)] Thioketal can be removed with a mercury salt. [H. Zinner, K. H. Rohde and A. Mattheus; Ann., 677, 160 (1964). E. J. Corey and R. B. Mitra; J. Am. Chem. Cos., 84, 2938 (1962)]

The isolation of the product can be carried out in a conventional manner. For example, well-refined 5-carboxy-2-acetylthiophene, which sometimes precipitates when the reaction system is diluted with, for example, water and, if necessary, acidified with a suitable acid such as hydrochloric acid, can be isolated by filtration and washing with water, or it may be isolated by extracting with an inert solvent such as ether or by evaporating the solvent and washing the product with water.

5-acetyl-2-thienylacetic acid and the compound of the formula (III) can be prepared from 2-thienylacetic acid as follows:

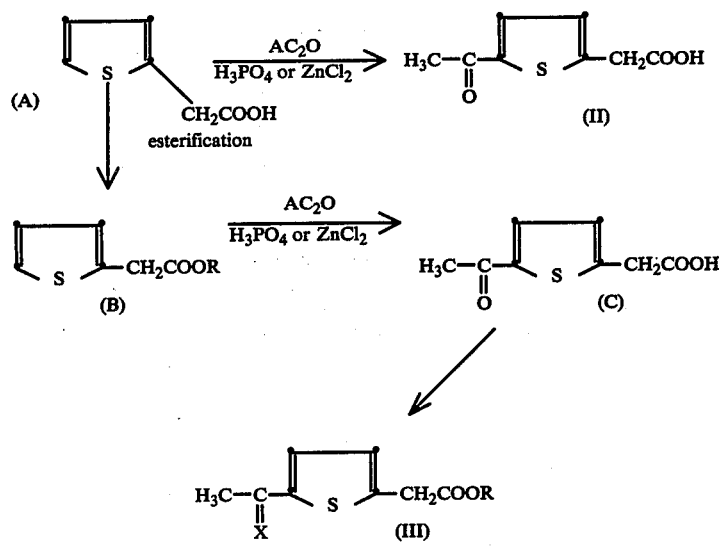

The compound (II) can be prepared by acylating 2-thienylacetic acid (A) with acetic anhydride in the presence of phosphoric acid or zinc chloride. The compound (C) can be obtained in the same manner as above from the compound (B), which can be prepared by the esterification of the compound (A). The compound (III) can be prepared by introducing the carbonyl protecting group by a conventional method as disclosed in the "Protective Groups in Organic Chemistry".

As mentioned previously, 5-carboxy-2-acetylthiophene can be used as an intermediate for the production of a therapeutic agent, which can be prepared from 5-carboxy-2-acetylthiophene as follows:

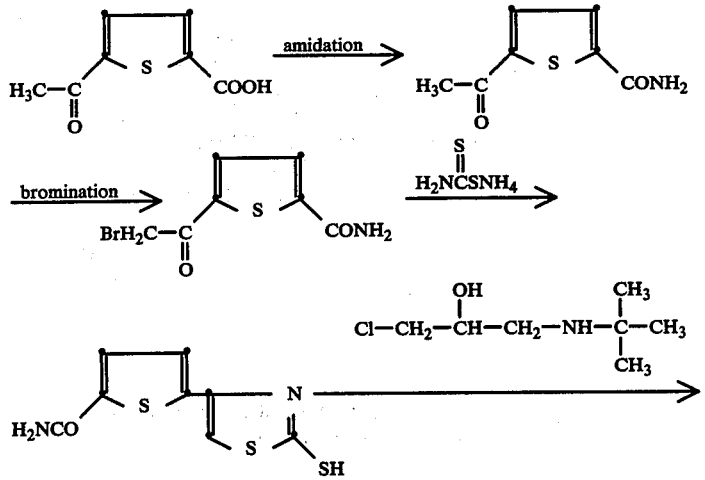

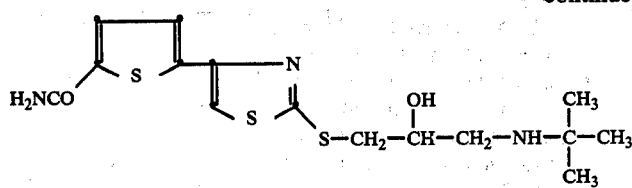

The following examples are given to illustrate the present invention more concretely, but it is not intended to limit the present invention thereto.

EXAMPLE 1

To an aqueous solution (5.3 g.) of sodium hypochlorite containing excess sodium hydroxide (prepared from one part of chlorine and 2.5 parts of sodium hydroxide) was added a solution of 0.204 g. of 5-acetyl-2-thienylacetic acid methyl ester ketal in 5 ml of ethanol dropwise at such a rate that the temperature could be maintained below 40° C. by means of a cooling bath. After the addition was completed, stirring was continued until the temperature fell to 25°–30° C. without the aid of the cooling bath (0.5–4 hrs.). Sodium bisulfite was added to destroy an excess of sodium hypochlorite. The resulting solution was made acidic with conc. hydrochloric acid (pH 1), diluted with 30 ml of water and extracted with ether. Ether layer was washed with water, dried and stripped to provide the residue, which was recrystallized from water to afford 0.12 g. (78.2%) of 5-carboxy-2-acetyl thiophene. This product was identified with an authentic sample prepared according to the known procedure. (IR, NMR and mixed m.p.)

EXAMPLE 2

In a mixture of acetic acid (8 ml) and acetic anhydride (2 ml) was dissolved 0.3 g. (0.003 mol) of $CrO_3$ and 0.186 g. (0.001 mol) of 5-acetyl-2-thienylacetic acid was added portionwise with mechanical stirring and cooling at 10° C. The resulting mixture was stirred at room temperature for 3.5 hrs. and diluted with 20 ml of water followed by extraction with ether. Ether layer was washed with water, dried and evaporated. The crude product was recrystallized from water to provide 0.13 g. (76%) of 5-carboxy-2-acetyl thiophene, identical to an authentic sample. (IR, NMR and mixed m.p.)

EXAMPLE 3

Chromic anhydride, 0.342 g. (0.00342 mol) was added portionwise to cooled (0°–5° C.) pyridine (10 ml). After a few minutes, orange complex began to precipitate. 5-Acetyl-2-thienylacetic acid, 0.202 g. (0.0011 mol) was added and stirred at room temperature overnight. The reaction mixture was made acidic with conc. hydrochloric acid and extracted with ether. Ether layer was washed with water, dried and evaporated. Crude product was purified by recrystallization from water. Yield; 0.14 g. (75.1%). This material was identified with an authentic sample. (IR, NMR and mixed m.p.)

EXAMPLE 4

To a solution of 5-acetyl-2-thienylacetic acid, 9.985 g. (0.0543 mol) in 90 ml of acetic acid was added potassium dichromate portionwise at 60° C. with stirring. After the addition was complete, the mixture was warmed up to 80° C. and 30 ml of acetic anhydride was slowly added thereto dropwise while the temperature of the reaction mixture rose gradually to reflux. The resulting solution was heated under reflux for 4 hrs. and cooled to 15° C. The green precipitate was removed by filtration and the filtrate was diluted with large volume of water. Precipitate was collected, washed with water and dried. Yield; 3.81 g. (41.3%). The material was identical to an authentic sample. (IR, NMR and mixed m.p.)

Preparation of 5-acetyl-2-thienylacetic acid methyl ester

A mixture of 2-thienylacetic acid methyl ester, 1.41 g. (0.01 mol) and acetic anhydride, 4.2 g. (0.04 mol) was heated at 70°–80° C. and 0.2 g. of 85% $H_3PO_4$ was added dropwise with mechanical stirring. The reaction was somewhat exothermic but cooling was not necessary. The mixture was maintained between 70°–80° C. for 3 hrs., and then, poured onto ice-water followed by extraction with ether. Organic layer was washed with water several times, dried over anhyd. $MgSO_4$ and evaporated. The residue was distilled at 2 mmHg and a fraction between 160° C. and 172° C. was collected. This material was gradually crystallized and could be recrystallized from the mixture of light-petroleum and benzene. m.p. 43°–44° C. Yield; 1.39 g. (76.5%)

Ketalization of 5-acetyl-2-thienylacetic acid methyl ester

A solution of ethyleneglycol, 0.997 g. (15.7 mmol) ethyl orthoformate, 1.307 g. (9.47 mmol), 5-acetyl-2-thienylacetic acid methyl ester, 0.572 g. (3.14 mmol) and a trace of p-toluenesulfonic acid was allowed to stand at room temperature for 3 hrs. The mixture was poured into water and the organic layer was separated. The aqueous layer was extracted with benzene (50 ml × 2). Both organic layers were combined, washed with water, dried over anhyd. $MgSO_4$ and evaporated in vacuo to provide 0.286 g. (91%) of the ketal as a yellow oil. This product can be characterized as the ethylene ketal of 5-acetyl-2-thienylacetic acid methyl ester on the basis of disappearance of carbonyl absorbtion at 1670 $cm^{-1}$ (IR) and appearance of singlet of dioxolane methylene at 4.00 (δ) (NMR).

What is claimed is:
1. A process for producing 5-carboxy-2-acetylthiophene which comprises
oxidizing a compound of the formula

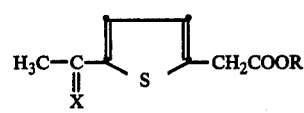

wherein X is a conventional carbonyl-protecting group and R is a conventional ester residue, with a hypohalite in a mixture of water and an alcohol at a temperature from 0° to 60° C., and then removing the carbonyl-protecting group.

2. A process for producing 5-carboxy-2-acetylthiophene which comprises oxidizing a compound of the formula

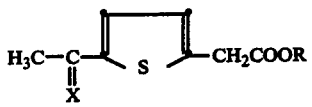

wherein X is a carbonyl oxygen protected with a ketal, hemithioketal, dithioketal, thiazolidine, imidazolidine or oxazolidine and R is lower alkyl or phenyl, with a hypohalite in a mixture of water and an alcohol at a temperature from 0° to 60° C., and then removing the protecting group.

3. The process according to claim 2, wherein the hypohalite is a hypochlorite.

4. The process according to claim 2, wherein the hypohalite is sodium hypochlorite, sodium hypobromite, potassium hypochlorite or potassium hypobromite.

5. A process for producing 5-carboxy-2-acetylthiophene which comprises oxidizing 5-acetyl-2-thienylacetic acid with a chromic anhydride-acetic acid complex, a chromic anhydride-pyridine complex, a chromic anhydride-dimethylformamide complex or a dichromate, in a solvent at a temperature from 0° to 100° C.

6. The process according to claim 5, wherein said dichromate is potassium dichromate or sodium dichromate.

7. The process according to claim 5, wherein said oxidation is carried out with a chromic anhydride-acetic acid complex or a chromic anhydride-pyridine complex in acetic acid, acetic anhydride, acetic acid-acetic anhydride mixed solvent, or pyridine.

8. The process according to claim 5, wherein said oxidation is carried out with a dichromate in acetic acid, acetic anhydride or a mixture thereof.

9. The process according to claim 8, wherein said dichromate is potassium dichromate or sodium dichromate.

* * * * *